United States Patent [19]
Künzler

[11] Patent Number: 5,914,355
[45] Date of Patent: Jun. 22, 1999

[54] METHOD FOR MAKING CONTACT LENSES HAVING UV ABSORBING PROPERTIES

[75] Inventor: Jay F. Künzler, Canandaigua, N.Y.

[73] Assignee: Bausch & Lomb Incorporated, Rochester, N.Y.

[21] Appl. No.: 09/079,781

[22] Filed: May 15, 1998

[51] Int. Cl.⁶ .............................. C08F 226/06; G02C 7/04
[52] U.S. Cl. ................. 523/106; 523/107; 526/261; 526/316; 264/1.38; 264/2.5; 264/2.6; 351/160 R
[58] Field of Search ................................. 523/106, 107; 526/261, 316; 264/1.38, 2.5, 2.6

[56] References Cited

U.S. PATENT DOCUMENTS

| | | | |
|---|---|---|---|
| 3,159,646 | 12/1964 | Milionis et al. | 260/308 |
| 3,408,429 | 10/1968 | Wichterle | 264/1 |
| 3,660,545 | 5/1972 | Wichterle | 264/1 |
| 3,761,272 | 9/1973 | Mannens et al. | 96/84 |
| 4,113,224 | 9/1978 | Clark et al. | 249/105 |
| 4,197,266 | 4/1980 | Clark et al. | 264/1 |
| 4,304,895 | 12/1981 | Loshaek | 526/313 |
| 4,486,504 | 12/1984 | Chung | 524/800 |
| 4,528,311 | 7/1985 | Beard et al. | 524/91 |
| 4,716,234 | 12/1987 | Dunks et al. | 548/259 |
| 4,719,248 | 1/1988 | Bambury et al. | 523/108 |
| 4,997,897 | 3/1991 | Melpolder | 526/284 |
| 5,034,461 | 7/1991 | Lai et al. | 525/100 |
| 5,135,965 | 8/1992 | Tahan | 523/106 |
| 5,271,875 | 12/1993 | Appleton et al. | 264/2.3 |
| 5,420,324 | 5/1995 | Lai et al. | 556/419 |
| 5,496,871 | 3/1996 | Lai et al. | 523/107 |
| 5,610,252 | 3/1997 | Bambury et al. | 526/279 |

OTHER PUBLICATIONS

Dr. R. Olson, "UV Absorber Progenitors: Photo–Fries Rearrangements of Sulfonate Esters of Hydroxphenylbenzotriazoles", Journal of Applied Polymer Science, vol. 28, 1159–1165 (1983).

U.S. application No. 09/079,701, Lai, filed May 15, 1998.
U.S. application No. 09/079,781, Kunzer, filed May 15, 1998.

Primary Examiner—Andrew E. C. Merriam
Attorney, Agent, or Firm—John E. Thomas; Denis A. Polyn

[57] ABSTRACT

A method for preparing a lens having UV-absorbing properties involves charging to a mold a monomer mixture comprising lens-forming monomers and an essentially non-UV-absorbing compound, and curing the monomer mixture to form a lens, followed by treating the lens to convert the essentially non-UV-absorbing compound to a UV-absorbing agent.

18 Claims, No Drawings

METHOD FOR MAKING CONTACT LENSES HAVING UV ABSORBING PROPERTIES

BACKGROUND OF THE INVENTION

The present invention relates to a method for preparing contact lenses containing an ultraviolet-absorbing agent, and capable of absorbing UV radiation, wherein the lens-forming monomer mixture is cured by exposure to UV light.

Lenses such as contact lenses or intraocular lenses may include a UV-absorbing agent in the lens to absorb light in the ultraviolet region of the spectrum, more particularly, to absorb light in the region of about 200 to 400 nm and, especially, about 290 to 400 nm. Representative UV-absorbing materials for such lens applications are described in U.S. Pat. Nos. 4,304,895 (Loshaek), 4,528,311 (Beard et al.) and 4,719,248 (Bambury et al.).

Generally, such lenses are formed by free radical polymerization of a monomer mixture including desired lens-forming monomers, usually in the presence of heat (thermal polymerization) or a light source (photopolymerization). One particular method for producing contact lenses involves thermal polymerization of the initial monomeric mixture in tubes in a heated water bath to provide rod-shaped articles, which rods are then cut into buttons, the buttons then being lathed into contact lenses; such methods for forming lenses including a UV absorbing agent are illustrated in the aforementioned U.S. Pat. Nos. 4,304,895 (Loshaek) and 4,528,311 (Beard et al.). Other methods involve casting the lenses directly in molds, wherein the monomer mixture is charged to the mold and polymerized by exposure to ultraviolet radiation.

In the case where it is desired to form lenses by a photopolymerization process, UV curing (i.e., exposure of the monomer mixture to radiation mainly in the ultraviolet region) of the monomer mixtures has proved very effective. It is also possible to effect photopolymerization using a light source also including light in the visible region of the spectrum, although light in this region is generally less efficient in effecting polymerization of conventional lens-forming monomer mixtures than UV curing. However, for lenses including a UV absorbing agent, problems are encountered when attempting to cure the monomer mixtures since this agent absorbs UV light, thus diminishing the amount of UV light available to effect polymerization and resulting in effective or uneven curing of the monomer mixture.

Accordingly, it would be desirable to provide a method whereby lenses exhibiting effective UV-absorbing properties can be polymerized by conventional free radical photopolymerization methods. The present invention provides such a method and solves the aforementioned problems.

SUMMARY OF THE INVENTION

The invention provides a method for preparing a lens having UV-absorbing properties, comprising charging to a mold a monomer mixture comprising lens-forming monomers and an essentially non-UV-absorbing compound, and curing the monomer mixture to form a lens; and treating the lens to convert the essentially non-TV-absorbing compound to a UV-absorbing agent.

Preferably, the lens is a contact lens or an intraocular lens, most preferably a hydrogel contact lens.

Preferred compounds included in the monomer mixture, and which are essentially non-UV absorbing but capable of converting to a UV-absorbing agent, are compounds of the formula:

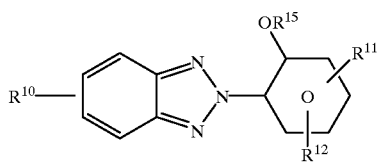

wherein each of $R^{10}$, $R^{11}$ and $R^{12}$ is independently hydrogen or a substituent; and $R^{15}$ is a protective radical that renders the compound essentially non-UV-absorbing. Especially preferred are compounds of the formula wherein at least one of $R^{11}$ and $R^{12}$ is a polymerizable ethylenically unsaturated radical, as well as compounds wherein $R^{15}$ is —$COCH_3$.

DETAILED DESCRIPTION OF PREFERRED EMBODIMENTS

The monomer mixtures employed in the invention include conventional lens-forming monomers.

The lens-forming monomers are monomers that are polymerizable by free radical polymerization, generally including an activated unsaturated radical, and most preferably an ethylenically unsaturated radical. (As used herein, the term "monomer" denotes relatively low molecular weight compounds that are polymerizable by free radical polymerization, as well as higher molecular weight compounds that are polymerizable by free radical polymerization and also referred to as "prepolymers", "macromonomers", and related terms.)

An especially preferred class of materials are hydrogel copolymers. A hydrogel is a crosslinked polymeric system that can absorb and retain water in an equilibrium state. Accordingly, for hydrogels, the monomer mixture will typically include at least one hydrophilic monomer and a crosslinking agent (a crosslinker being defined as a monomer having multiple polymerizable functionalities). Suitable hydrophilic monomers include: unsaturated carboxylic acids, such as methacrylic and acrylic acids; acrylic substituted alcohols, such as 2-hydroxyethylmethacrylate and 2-hydroxyethylacrylate; vinyl lactams, such as N-vinyl pyrrolidone; and acrylamides, such as methacrylamide and N,N-dimethylacrylamide. Typical crosslinking agents include polyvinyl, typically di- or tri-vinyl monomers, such as di- or tri(meth)acrylates of diethyleneglycol, triethyleneglycol, butyleneglycol and hexane-1,6-diol; divinylbenzene; and others known in the art.

Another preferred class of lens-forming monomers are those that form silicone hydrogel copolymers. Such systems include, in addition to a hydrophilic monomer, a silicone-containing monomer. One suitable class of silicone containing monomers include known bulky, monofunctional polysiloxanylalkyl monomers represented by Formula (I):

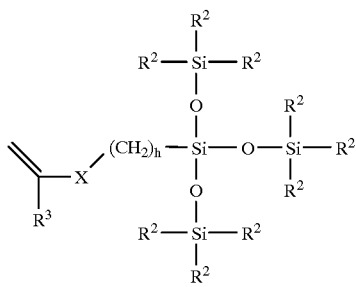
(I)

wherein:

X denotes —COO—, —CONR⁴—, —OCOO—, or —OCONR⁴— where each where R⁴ is H or lower alkyl; R³ denotes hydrogen or methyl; h is 1 to 10; and each R² independently denotes a lower alkyl or halogenated alkyl radical, a phenyl radical or a radical of the formula

wherein each R⁵ is independently a lower alkyl radical or a phenyl radical. Such bulky monomers specifically include methacryloxypropyl tris(trimethylsiloxy)silane, pentamethyldisiloxanyl methylmethacrylate, tris(trimethylsiloxy) methacryloxy propylsilane, methyldi(trimethylsiloxy) methacryloxymethyl silane, 3-[tris(trimethylsiloxy)silyl] propyl vinyl carbamate, and 3-[tris(trimethylsiloxy)silyl] propyl vinyl carbonate.

Another suitable class are multifunctional ethylenically "end-capped" siloxane-containing monomers, especially difunctional monomers represented Formula (II):

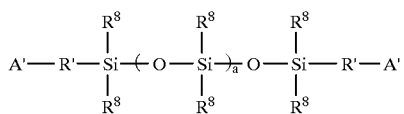
(II)

wherein:

each A' is independently an activated unsaturated group;

each R' is independently are an alkylene group having 1 to 10 carbon atoms wherein the carbon atoms may include ether, urethane or ureido linkages therebetween;

each R⁸ is independently selected from monovalent hydrocarbon radicals or halogen substituted monovalent hydrocarbon radicals having 1 to 18 carbon atoms which may include ether linkages therebetween, and a is an integer equal to or greater than 1. Preferably, each R⁸ is independently selected from alkyl groups, phenyl groups and fluoro-substituted alkyl groups. It is further noted that at least one R⁸ may be a fluoro-substituted alkyl group such as that represented by the formula:

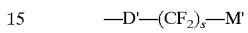

wherein:

D' is an alkylene group having 1 to 10 carbon atoms wherein said carbon atoms may include ether linkages therebetween;

M' is hydrogen, fluorine, or alkyl group but preferably hydrogen; and s is an integer from 1 to 20, preferably 1 to 6.

With respect to A', the term "activated" is used to describe unsaturated groups which include at least one substituent which facilitates free radical polymerization, preferably an ethylenically unsaturated radical. Although a wide variety of such groups may be used, preferably, A' is an ester or amide of (meth)acrylic acid represented by the general formula:

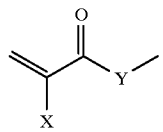

wherein X is preferably hydrogen or methyl, and Y is —O— or —NH—. Examples of other suitable activated unsaturated groups include vinyl carbonates, vinyl carbamates, fumarates, fumaramides, maleates, acrylonitryl, vinyl ether and styryl. Specific examples of monomers of Formula (II) include the following:

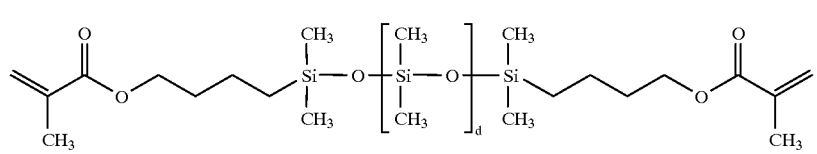
(IIa)

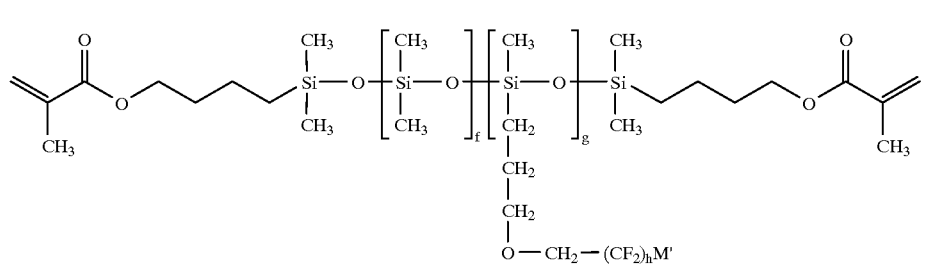
(IIb)

-continued (IIc)

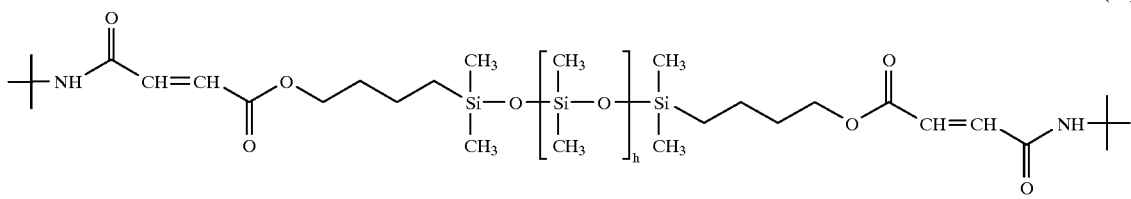

wherein:

d, f, g, h and k range from 0 to 250, preferably from 2 to 100; and

M' is hydrogen or fluorine.

Other silicone-containing monomers include the silicone-containing monomers described in U.S. Pat. Nos. 5,034,461, 5,610,252 and 5,496,871, the disclosures of which are incorporated herein by reference. Many other silicone-containing monomers are well-known in the art.

As mentioned, polymerization (or curing) of monomer mixtures to form lenses by exposure of the monomer mixture to ultraviolet radiation has proved very effective, however, for lenses including a UV-absorbing agent, problems are encountered when attempting to conduct polymerization of the monomer mixture by exposure to ultraviolet radiation since this agent absorbs UV light. The invention provides a method whereby lenses with UV-absorbing properties can be prepared by conventional methods involving free radical polymerization.

More specifically, to the monomer mixture including the lens-forming monomers is added a compound that is essentially non-UV-absorbing but can subsequently be converted to a UV absorbing agent in a post-polymerization process, i.e., after the lens has been cured, for example, photopolymerized by UV curing. As used herein, the term "UV-absorbing agent" denotes an agent that, when incorporated in a film of the lens-forming monomers having a 0.02-mm thickness, is capable of reducing the transmittance of light in the region of 320 to 400 nm to at least 50 percent of a similar sample lacking the UV-absorbing agent, and preferably, to at least 70 percent, most preferably to at least 85 percent. It is also preferred that such a sample incorporating the UV-absorbing agent transmits no more than 70% of light in the region of 320 to 400 nm and no more than 90% of light in the region of 290 to 320 nm. The term "essentially non-UV-absorbing agent" denotes an agent that, if incorporated in such a film sample, is capable of reducing the transmittance of light in the region of 320 to 400 nm to no more than 40 percent of a similar sample lacking this agent (and preferably, no more than that 20 percent).

One preferred class of UV-absorbing agents known for contact lens and intraocular lens applications includes benzotriazoles that contain a phenol moiety. Examples of such benzotriazoles are described in U.S. Pat. Nos. 4,528,311 (Beard et al.), 4,716,234 (Dunks et al.), 4,719,248 (Bambury et al.), 3,159,646 (Milionis et al.) and 3,761,272 (Manneus et al.), the disclosures of which are incorporated herein by reference. Specific examples include 2-(2'-hydroxy-5'-methacrylamidophenyl)-5-chlorobenzotriazole, 2-(2'-hydroxy-5'-methacrylamidophenyl)-5-methoxybenzotriazole, 2-(2'-hydroxy-5'-methacryloxypropyl-3'-t-butyl-phenyl)-5-chlorobenzotriazole, 2-(2'-hydroxy-5'-methacryloxyethylphenyl)benzotriazole, 2-(2'-hydroxy-5'-methacryloxypropylphenyl)benzotriazole. These benzotriazoles may be represented by the general formula (I):

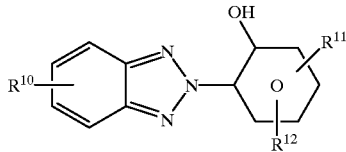

wherein $R^{10}$ may be hydrogen or a substituent (representative substituents being selected from the group consisting of halogen, $C_1$–$C_4$ alkyl and $C_1$–$C_4$ alkoxy); and each of $R^{11}$ and $R^{12}$ independently may be hydrogen or a substituent (representative substituents being selected from the group consisting of halogen, $C_1$–$C_4$ alkyl and $C_1$–$C_4$ alkoxy). Preferably, at least one of $R^{11}$ or $R^{12}$ is a polymerizable ethylenically unsaturated moiety, such as

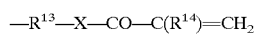

wherein $R^{13}$ is a single bond or $C_1$–$C_{10}$ alkylene, X is —O— or —NH—, and $R^{14}$ is hydrogen or methyl.

The essentially non-UV-absorbing agent that is actually incorporated in the initial monomer mixture, along with the lens-forming monomers, is a derivative of the UV-absorbing agent where the hydroxyl radical of the phenol moiety is replaced with a protective group, such protective group rendering the agent essentially non-UV absorbing (i.e., the protective group essentially shifts the absorption properties of the compound so that the agent does not absorb as strongly in the 320 to 400 nm range). This protective group can be converted back to a hydroxyl radical after the lens is cured, thus rendering the lens UV-absorbing.

For the preferred benzotriazoles, the agents that are derivatives of the Formula (I) compounds and that are added to the initial monomer mixture, may be represented by the general formula (Ia):

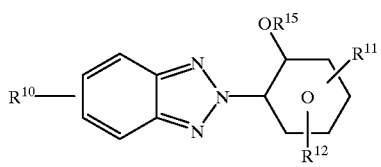

wherein $R^{10}$, $R^{11}$ and $R^{12}$ have the same meanings as for Formula (I) and $R^{15}$ is the protective group that can be converted back to the hydroxyl radical in a post-polymerization treatment process. Preferably, at least one of $R^{11}$ or $R^{12}$ in Formula (Ia) is a polymerizable ethylenically unsaturated moiety, such as

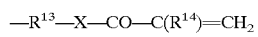

Specific examples of the —$R^{15}$ radical include: acetyl (—$COCH_3$), alkylsilanes such as —O—$Si(CH_2CH_3)_3$; alkyl ethers such as methoxy; and alkyl esters, such as methylcarbonyloxy and methycarbonate. It is understood, however, that any suitable phenol protecting radical available in the art may be used.

The agents of Formula (Ia) may be prepared by methods generally known in the art. In the case where the protective group is —$COCH_3$, a compound of Formula (I) can be reacted with acetic anhydride. In the case where the protective group is an alkyl silane, a compound of Formula (I) can be reacted with a chlorotrialkylsilane, such as chlorotriethylsilane. In the case where the protective group is an alkyl ether, a compound of Formula (I) can be reacted with chloroalkylether, such as chloromethyl methyl ether. In the case where the protective group is an alkylcarbonate, a compound of Formula (I) can be reacted with vinylchloroformate. Representative detailed syntheses of the Formula (Ia) compounds is provided in the examples, below.

Another representative class of UV-absorbing agents are benzophenone UV-absorbers containing a phenolic radical. Specific examples are 2,2-dihydroxy-4,4-dimethoxybenzophenone, 2,2-dihydoxy-4-methoxy-benzophenone, and the polymerizable benzophenones described in U.S. Pat. Nos. 4,304,895 (Loshaek) the disclosure of which is incorporated herein by reference. Accordingly, the derivatives of these UV-absorbing agents, that are incorporated in the initial monomer mixture in practice of this invention, are benzophenone derivatives where at least one hydroxyl radical of the phenolic radical is replaced with one of the aforementioned protective groups, for example, an acetyl radical.

Especially preferred for contact lens and intraocular lens applications are agents that include a polymerizable ethylenically unsaturated moiety. For example, as mentioned for the benzotriazoles of Formula (Ia), preferred agents include those with at least one ethylenically unsaturated radical. These agents copolymerize with the lens-forming monomers, i.e., the agent forms an integral part of the copolymer network. Surprisingly, it has been found that even though these compounds copolymerize with the lens-forming monomers, the protected radical is still able to be converted back to a phenolic moiety, thus rendering the compounds effective as UV-absorbing agents.

The agents convertible to UV-absorbing agents will generally be included in the monomer mixture at about 0.1 to about 5 weight percent, more preferably about 0.2 to about 2 weight percent.

The monomer mixtures may further include a tinting agent that imparts some degree of color to the lens. The monomer mixtures will generally include a polymerization initiator, such as commercial acetophenone-based initiators, titanocene-based initiators, and/or aromatic phosphine oxide-based initiators available under the Darocur or Irgacur tradenames.

Generally, the monomer mixture, containing the lens-forming monomers and the protected essentially non-UV-absorbing agent, is charged to a mold, and then subjected to light to effect curing of the monomer mixture in the mold. Various processes are known for curing a monomeric mixture in the production of contact lenses, including spincasting and static casting. Spincasting methods involve charging the monomer mixture to a mold, and spinning the mold in a controlled manner while exposing the monomer mixture to light. Static casting methods involve charging the monomer mixture between two mold sections, one mold section shaped to form the anterior lens surface and the other mold section shaped to form the posterior lens surface, and curing the monomer mixture by exposure to light. Such methods are described in U.S. Pat. Nos. 3,408,429, 3,660,545, 4,113,224, 4,197,266, and 5,271,875.

Following casting of the lenses, the cured lens is treated to remove the phenol protective group, i.e., to convert this radical to hydroxyl. Various methods can be used to carry out this "deprotection" process, examples including: immersing the lens in a borate-buffered solution; immersing the lens in a saturated bicarbonate solution; or immersing the lens in a solution of bicarbonate and lower alcohol. If desired, this treatment can be conducted at elevated temperature to decrease time required for the treatment. A further advantage of the invention is that this deprotection post-treatment can be accomplished by heating the lens while immersed in a buffered saline solution, a process that is conventionally performed on contact lenses as part of the sterilization process, thereby avoiding the need for a supplemental step in the overall manufacturing process.

The following examples illustrate various preferred embodiments.

EXAMPLE 1

Synthesis of Acetyl Protected 2-[3-(2H-Benzotriazol-2-yl)-4-Hydroxyphenyl]Ethyl Methacrylate To a 250 mL one-neck round bottom fitted with a magnetic stirrer is added (20.0 g, 0.192 mmole), acetic anhydride (50 g, mole) and dimethylaminopyridine (10.4 g, 68.0 mmol). The reaction is stirred for 48 hours at which time 200 ml of ethyl acetate is added and the solution is washed five times with brine. The organic layer is collected, dried over magnesium sulfate, filtered and rotoevaporated to an oil using an air bleed and a maximum temperature of 40° C. to minimize polymer formation. The oil is purified by fractional column chromatography (250 g silica gel/methylene chloride as eluant) resulting in 16.5 g (purity of 99.0% by liquid chromatography) of acetyl protected 2-[3--(2H-Benzotriazol-2-yl)-4-hydroxyphenyl]ethyl methacrylate.

EXAMPLE 2

UV Spectra Data

The UV spectra of the compound prepared in Example 1 was compared with the UV spectra of its parent compound (a compound of Formula (I), 2-(2'-hydroxy-5'-methacryloxyethylphenyl)benzotriazole)) by diluting each compound in a solvent at a 1:100,000 dilution ratio, and measuring the amount of light absorption. Whereas the parent compound exhibited a sharp absorption peak at about 350 nm, the compound of Example 1 exhibited no such peak, instead having a well-defined absorption peak at about 300 nm, indicating that addition of the acetyl-protective group was effective at shifting significantly the UV absorbance to a lower wavelength.

EXAMPLE 3

The compound of Example 1 was added at 0.8 weight percent to a monomer mixture of 2-hydroxyethylmethacrylate (Hema), ethyleneglycoldimethacrylate (EGDMA, a crosslinker), benzoin methyl ether (BME, an initiator) and glycerin (a diluent). For comparative purposes, the compound 2-(2'-hydroxy-5'-methacryloxyethylphenyl) benzotriazole) was added at 0.8 weight percent to the same base monomer mixtures. Both resultant mixtures were cast between two glass plates and exposed to UV light (2500 $\mu W/cm^2$) for one hour. Whereas the mixture containing the compound of Example 1 was effectively polymerized within 10 minutes to form a film, the comparative mixture, containing the conventional UV-absorbing agent, failed to polymerize.

EXAMPLE 4

The compound of Example 1 was added at 0.4 weight percent and 0.8 weight percent to same Hema-based monomer mixture described in Example 3. Both resultant mixtures were cast between two glass plates and exposed to UV light (2500 $\mu$W/cm$^2$) for one hour. The resultant cured films were subjected to a series of deprotection schemes, including: autoclaving in borate-buffered solution; autoclaving in saturated bicarbonate; soaking in saturated bicarbonate solution at room temperature; and soaking in 50/50 solution of methanol/saturated bicarbonate. The treated films were compared with a film prepared by thermal curing the compound 2-(2'-hydroxy-5'-methacryloxyethylphenyl) benzotriazole) (0.8 weight percent) added to the same base monomer mixture. For all treated films, the acetyl group was effectively removed, as these films had UV absorbing properties characteristic of the thermally cured films based on the UV absorbing parent compound.

EXAMPLE 5

The compound of Example 1 was added at 0.8 weight percent (wt %) to a monomer mixture composed mainly of the following: 20 wt % of a fumarate-capped polysiloxanediol-based prepolymer (Formula (IIc) wherein h is about 20); 40 wt % methacryloxypropyl tris (trimethylsiloxy)silane; and 40 wt % N,N-dimethylacrylamide. The resultant mixture was cast between two glass plates and exposed to UV light (2500 $\mu$W/cm$^2$) for one hour. The resultant cured films were subjected to a series of deprotection schemes as in Example 4. It was found that soaking in 50/50 solution of methanol/saturated bicarbonate successfully converted the compound to a UV-absorbing agent.

EXAMPLE 6

The compound of Example 1 was added at 0.8 weight percent to a monomer mixture composed mainly of 2-hydroxyethylmethacrylate, N-vinylpyrrolidone, crosslinking monomers and 4-t-butyl-2-hydroxycyclohexylmethacrylate. The resultant mixture was placed on the molding surface of a first plastic mold section, shaped to provide an anterior contact lens surface, and a second plastic mold section having a molding surface shaped to provide a posterior contact lens surface was placed on the first mold section, the monomer mixture being contained in the mold cavity formed between these two molding surfaces. This assembly was then subjected to UV curing. The two mold sections were then immediately separated, lenses were released from the mold section, and equilibrated in borate buffered saline. Upon autoclaving, the compound was converted to a UV-absorbing agent, as the lenses exhibited UV absorbing properties.

Many other modifications and variations of the present invention are possible to the skilled practitioner in the field in light of the teachings herein. It is therefore understood that, within the scope of the claims, the present invention can be practiced other than as specifically described.

I claim:

1. A method for preparing a lens having UV-absorbing properties, comprising:

charging to a mold a monomer mixture comprising lens-forming monomers and an essentially non-UV-absorbing compound, and curing the monomer mixture to form a lens; and treating the lens to convert the essentially non-UV-absorbing compound to a UV-absorbing agent.

2. The method of claim 1, wherein the lens-forming monomers include a hydrophilic monomer and a crosslinking monomer.

3. The method of claim 1, wherein the lens-forming monomers include a hydrophilic monomer and a silicone-containing monomer.

4. The method of claim 1, wherein the monomer mixture includes a polymerization initiator.

5. The method of claim 1, wherein the lens is a contact lens.

6. The method of claim 5, wherein the monomer mixture is cured in a mold cavity formed between a first mold section having a molding surface shaped to provide a posterior contact lens surface and a second mold section having a molding surface shaped to provide an anterior contact lens surface.

7. The method of claim 1, wherein the monomer mixture including the essentially non-UV-absorbing compound absorbs less than 50% of incident light at wavelengths ranging from 320 to 400 nm.

8. The method of claim 7, wherein the essentially non-UV-absorbing compound converts to a UV-absorbing agent such that the formed lens absorbs at least 50% of incident light at wavelengths ranging from 320 to 400 nm.

9. The method of claim 8, wherein the formed lens absorbs at least 70% of light in the region of 320 to 400 nm, and at least 90% of light in the region of 290 to 320 nm.

10. The method of claim 1, wherein the monomer mixture is cured by photopolymerization.

11. The method of claim 1, wherein the monomer mixture is cured by exposure to a light source including light in the UV region.

12. The method of claim 1, wherein the essentially non-UV-absorbing compound includes a polymerizable ethylenically unsaturated radical.

13. The method of claim 1, wherein the essentially non-UV-absorbing compound has the general formula:

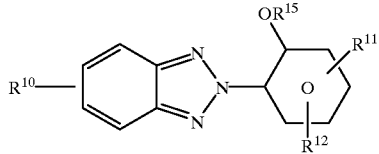

wherein each of $R^{10}$, $R^{11}$ and $R^{12}$ is independently hydrogen or a substituent selected from the group consisting of halogen, $C_1$–$C_4$ alkyl and $C_1$–$C_4$ alkoxy, provided that at least one of $R^{11}$ and $R^{12}$ may be a polymerizable ethylenically unsaturated radical; and $R^{15}$ is a phenolic protective radical that renders the compound essentially non-UV-absorbing.

14. The method of claim 13, wherein at least one of $R^{11}$ and $R^{12}$ is an ethylenically unsaturated radical of the formula

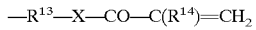

wherein $R^{13}$ is a single bond or $C_1$–$C_{10}$ alkylene, X is —O— or —NH—, and $R^{14}$ is hydrogen or methyl.

15. The method of claim 13, wherein $R^{15}$ is —COCH$_3$.

16. The method of claim 13, wherein the treatment of the lens converts the essentially non-UV-absorbing compound to the following:

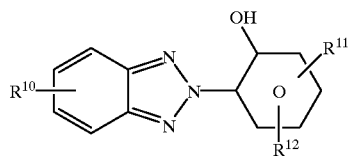

wherein each of $R^{10}$, $R^{11}$ and $R^{12}$ are the same as in claim 13.

17. The method of claim 1, wherein the essentially non-UV-absorbing compound includes a protected phenolic radical, and the treatment of the lens converts such radical to a phenol radical.

18. The method of claim 1, wherein treating of the lens includes immersing the lens in a solution and heating the solution.

* * * * *